United States Patent [19]

Bittle

[11] 4,287,178

[45] Sep. 1, 1981

[54] FELINE RHINOTRACHEITIS VACCINE AND PRODUCTION AND USE THEREOF

[75] Inventor: James L. Bittle, Doylestown, Pa.

[73] Assignee: Pitman-Moore, Inc., Washington Crossing, N.J.

[21] Appl. No.: 90,849

[22] Filed: Nov. 2, 1979

Related U.S. Application Data

[63] Continuation of Ser. No. 454,345, Mar. 25, 1974, abandoned.

[51] Int. Cl.³ .................... A61K 39/12; A61K 39/265
[52] U.S. Cl. ..................................... 424/89; 435/237
[58] Field of Search ................... 424/89; 435/235–239

[56] References Cited

U.S. PATENT DOCUMENTS

| | | | |
|---|---|---|---|
| 3,293,130 | 12/1966 | Slater et al. | 424/89 |
| 3,520,972 | 7/1970 | Smith et al. | 424/89 |
| 3,562,387 | 2/1971 | Lauerman | 424/89 |
| 3,709,782 | 1/1973 | Smith et al. | 424/89 |
| 3,733,401 | 5/1973 | Suida | 424/89 |
| 3,869,547 | 3/1975 | Mebus et al. | 424/89 |
| 3,892,627 | 7/1975 | Simons et al. | 424/89 |
| 3,937,812 | 2/1976 | Bittle et al. | 424/89 |
| 3,944,469 | 3/1976 | Bittle et al. | 424/89 |
| 4,021,302 | 5/1977 | Smith et al. | 435/235 |
| 4,031,204 | 6/1977 | Davis | 424/89 |

FOREIGN PATENT DOCUMENTS

| | | | |
|---|---|---|---|
| 1174016 | 7/1964 | Fed. Rep. of Germany | 424/89 |
| 1617940 | 9/1970 | Fed. Rep. of Germany | 424/89 |
| 2512903 | 2/1975 | Fed. Rep. of Germany | 424/89 |
| 2702634 | 7/1978 | Fed. Rep. of Germany | 424/89 |
| 1426195 | 4/1966 | France | 424/89 |
| 1286250 | 8/1972 | United Kingdom | 424/89 |
| 1492930 | 11/1977 | United Kingdom | 424/89 |

OTHER PUBLICATIONS

Dubes et al., Virology, vol. 4, pp. 275–296 (1957).
Schwarz et al., Proc. Soc., Exp. Biol. & Med., vol. 96, pp. 453–458 (1957).
Wenner et al., Am J. Hyg., vol. 70, pp. 335–350 (1959).

*Primary Examiner*—Shep K. Rose
*Attorney, Agent, or Firm*—Millen & White

[57] ABSTRACT

The propagation and modification of feline viral rhinotracheitis (FVR) virus in feline tissue cultures and the development of a vaccine useful for the prevention of feline viral rhinotracheitis in cats, said vaccine comprising a modified FVR virus.

20 Claims, No Drawings

FELINE RHINOTRACHEITIS VACCINE AND PRODUCTION AND USE THEREOF

This is a continuation, Ser. No. 454,345 filed Mar. 25, 1974, now abandoned.

BACKGROUND OF THE INVENTION

Infectious feline viral rhinotracheitis is a specific, common and serious disease of cats caused by the feline herpesvirus known as feline viral rhinotracheitis (FVR) virus. Reports in the literature indicate that this disease is responsible for approximately half the clinical cases of feline respiratory infections. The virus infects the epithelial cells of the nose, pharynx, trachea and eye, causing epitheliolysis and necrosis. The ocular manifestations predominantly involve the conjunctiva; however ulcerative keratitis can develop. The virus is shed from the nose, eyes and mouth through the course of the clinical disease. FVR virus infections are often severe and the mortality may be significant, especially in young kittens. Abortion or generalized infection of newborn kittens may occur following infection of pregnant queens with the virus. The transmission of FVR virus to susceptible cats is generally by intranasal instillation, for example, by droplets expelled in sneezing or by contact (usually nose to nose). Resistance following recovery from natural or experimental infection is of short duration (1–3 months).

The causative virus of FVR was first isolated from infected cats by R. A. Crandell and F. D. Maurer, Proc. Soc. Exptl. Biol. and Med., 97, 487 (1958) and the name "feline viral rhinotracheitis" was first proposed for the disease by R. A. Crandell and E. W. Despeaux, Proc. Soc. Exptl. Biol. and Med., 101, 494 (1959). Since then, several reports have appeared in the literature which confirm the isolation of FVR virus from feline subjects in various parts of the world, which identify the virus as a feline member of the herpesvirus group, and which describe the transmission, epidemiology and histologic characteristics of the disease. For example, see J. L. Bittle et al., Amer. J. Vet. Res., 21, 547 (1960); R. A. Crandell et al., J.A.V.M.A., 138, 191 (1961); J. Ditchfield and I. Grinyer, Virology, 26 504 (1965); R. H. Johnson and R. G. Thomas, Vet. Rec., 79, 188 (1966); R. C. Povey, Vet Rec., 82, 335 (1969); T. E. Walton and J. H. Gillespie, Cornell Vet., 60, 232 (1970); Colloquium Report, J.A.V.M.A., 157, 2043 (1970); R. A. Crandell, J.A.V.M.A., 158, 922 (1971); and S. I. Bistner et al., J.A.V.M.A., 159, 1223 (1971). An excellent up to date review is provided by R. A. Crandell in the chapter entitled "Feline Viral Rhinotracheitis (FVR)" in the book "Advances in Veterinary Science and Comparative Medicine", Volume 17, Edtd. by C. A. Brandly and C. E. Cornelius, pages 201-24, Academic Press, Inc., New York, 1973.

Although attempts to produce a feline viral rhinotracheitis virus vaccine have been reported, none have proven successful. Investigators in England [Povey & Johnson, J. Small Anim. Pract., 11, 490 (1970)] reported failure in attempts at vaccine prophylaxis with a live, non-attenuated FVR virus vaccine given intramuscularly. Although they obtained a degree of success with formalinized and beta-propiolactone inactivated FVR virus vaccines in experimental cats, such vaccines failed to significantly reduce the incidence of disease in feline colonies. To date, no effective vaccine is available for protecting cats against FVR virus.

DESCRIPTION OF THE INVENTION

In accordance with the present invention, it has been found that FVR virus can be propagated in feline tissue cultures, preferably kidney and tongue, and the virulence of the virus so modified and reduced that no symptoms of the disease are observed upon parenteral inoculation.

Accordingly, the present invention produces a modified or attenuated strain of live, feline viral rhinotracheitis virus which when parenterally inoculated, preferably intramuscularly, into cats, it immunizes the cats to virulent FVR disease. A vaccine is also provided which is attenuated to an extent that will stimulate an antibody response effectively immunizing the cats for prolonged periods.

The vaccine is safe in that it will not cause any disease in cats that receive it by the parenteral route nor will the modified FVR virus pass from the vaccinated cat to other cats in contact with it, thereby eliminating the possibility of increasing the virulence of the virus by animal passage. This constitutes a significant advance in the control of FVR disease.

Live, virulent FVR virus can be obtained from cats infected with feline viral rhinotracheitis according to methods of isolation and identification described in the literature [e.g., see R. A. Crandell and F. D. Maurer, Proc. Soc. Exptl. Biol. & Med., 97, 487 (1958); J. L. Bittle et al., Amer. J. Vet. Res., 21, 547 (1960); and J. Ditchfield and I. Grinyer, Virology, 26, 504 (1965)]. In general, virus isolations can be made by swabbing the nasal and conjuntival membranes of infected cats with moist, sterile, cotton swabs which are then placed in a suitable feline tissue culture medium, followed by standard serial passages in order to replicate and isolate the virus. A particularly suitable culture medium is one derived from the cortical tissue of kidneys from 8- to 12-week old kittens which is trypsinized by a method similar to that described by J. Youngner [Proc. Soc. Exptl. Biol. & Med., 85, 202 (1954)] for monkey kidney cells.

In preparing the vaccines of this invention, it has been found that attenuation and modification of the virulent FVR virus can be readily accomplished by a relatively few, at least about 7, serial passages in feline tissue utilizing lower incubation temperatures of about $30° \pm 2°$ C., preferably about 32° C. Purification of the viral preparation may be accomplished by standard terminal dilution techniques, for example, tube or plaque methods, during or following the course of serial passages.

The FVR virus is capable of propagation in such feline tissue culture systems, for example, lung, testicle, kidney, thymus, tongue and embryonic fetal tissue, and also in established cell lines, such as, for example, Crandell's cat kidney cell line (CrFK), cat tongue cells at the third passage level (Fc3Tg) and feline neurofibrosarcoma cell line (FNFS). Feline tongue cell lines are most preferred.

The passage time intervals should be such as to sufficiently allow the virus to replicate between passages, preferably from 2 to 7 days. The optimum passage time interval can readily be determined by standard techniques, for example, by cytopathic observations, such as by allowing the virus to grow during a particular passage prior to the point where a gross cytopathic effect (CPE) can be observed while continuing incubation.

The obtention of successful vaccines by the present low temperature method is rather surprising in view of the known fact that serial passage in feline tissue at normal incubation temperatures, about 35°–37° C., does not alter or modify the virus or its pathogenicity even after 100 passages [R. A. Crandell, J.A.V.M.A., 158, 922 (1971)]. A shown hereafter (see Example III), however, subsequent modification of the virus can be accomplished by serial passages at lower incubation temperatures.

In accordance with this invention, therefore, a process is provided for attenuating virulent feline viral rhinotracheitis (FVR) virus for the production of a vaccine capable when injected into cats of immunizing them against FVR which comprises introducing an inoculum of virulent FVR virus into a nutrient fluid feline tissue culture medium which is non-toxic to said virus, propagating said virus by incubating said nutrient tissue culture medium at a temperature of about 30°±2° C. for a period of 2 to 7 days, and thereafter separating an inoculum of said virus and serially passing the virus through other such feline tissue cultures for a total of at least about 7 passages.

The viral preparations produced by this invention may be diluted to adjust their potency, and they may have added to them stabilizers, such as dextrose and lactose, or other non-toxic substances. The viral preparations may also be desiccated, e.g., by freeze drying, for storage purposes or for subsequent formulation into liquid vaccines. Stabilizers useful in the freeze drying of viruses are described in W. A. Rightsel et al., Cryobiology, 1967, 3:423 and D. Greiff et al., Advances in Freeze Drying, L. Rey, Ed., pp. 103–122, Hermann, Paris, 1966. In addition, the vaccines may be utilized in a mixture with other immunogenic vaccines for administration to cats.

The manner in which our invention is carried out is described in greater detail in conjunction with the following specific experiments. It is understood that these specific experiments are by way of illustration, and not by limitation.

EXAMPLE I

A sample of live virulent FVR virus cultured and isolated according to the procedure described by J. L. Bittle et al., Amer. J. Vet. Res., 21, 547, (1960) is added to monolayers of a feline diploid tongue cell line in tissue culture tubes (16×125 mm) prepared as follows. The tongue cell line used is the Fe3Tg line referred to in K. M. Lee et al., Cornell Veterinarian, 59, 539 (1969). Each cell line tube, containing 1–2 ml of growth medium consisting of Eagles Minimum Essential Medium (MEM) supplemented with 10% fetal calf serum, 0.1% lactalbumin hydrolysate, 30 units penicillin, 30 mcg streptomycin and 2.5 mcg amphotericin, is seeded with 1 ml feline tongue cells (200,000 cells per ml). If necessary, the pH is adjusted with sodium bicarbonate to maintain a pH of about 7.2–7.8. The cells in the tubes are allowed to grow at about 35°±2° C. until a monolayer of cells is achieved. Fluids are then poured off and 1–2 ml of a maintenance medium (same as above medium except that 1–2% fetal calf serum is utilized) is added. About 4 to 6 such tubes are utilized per viral passage.

To each tissue culture tube is added the FVR virus inoculum. The thus-seeded tube is maintained at 30°±2° C. until a cytopathic effect (CPE) is observed by microscopic examination (about 2–7 days). When the CPE reaches about 75–90% of the monolayer, the contents of the tube are harvested and 0.2 ml inoculums are subjected to identical serial passages for 6 additional passages (7 passages total). After the 7th passage, a standard terminal dilution purification is performed utilizing Eagles MEM supplemented with the aforementioned antibiotics (no serum) as the diluent with incubation maintained at 30°±2° C. After 7 days, the final tube which is positive with 75–90% CPE is harvested and the entire procedure repeated twice for a total of 10 passages. All 11th passage is performed for purposes of increasing volume by inoculating a 0.5 ml sample from the 10th passage into flasks containing mololayers of feline diploid tongue cell cultures obtained by propagation of the tongue cells as previously described. At the end of the 11th passage, the pool is harvested, identified and titrated by known methods.

The pool thus prepared constitutes a bulk vaccine which may be diluted according to the titer or may have added thereto stabilizers or other nontoxic substances. For use as a vaccine, it may be desiccated or it may be prepared in liquid form.

In propagating and attenuating the virus, any nontoxic nutrient fluid tissue culture medium may be utilized. In addition to the supplemented Eagles MEM medium described above, it will be understood that other nontoxic nutrient fluid tissue culture mediums may also be used.

EXAMPLE II

1 Ml of a vaccine prepared according to Example I and titrated to a virus titer at 35°±2° C. of $10^{4.5}$ TCID$_{50}$/ml (determined by CPE) is administered intramuscularly to three susceptible cats. Two other cats are maintained as unvaccinated controls. All 5 cats are previously determined to be sero-negative to FVR virus. Evidence of the disease (FVR) is generally observed from about the 4th through the 9th day after normal contact or challenge with virulent FVR virus. On the fourth day after vaccination, the negative results of a throat swab test on all 5 cats indicate an absence of shedding of the virus. The antibody titer of all 5 cats prior to vaccination is less that 1:2 and one month later, just prior to challenge, the antibody titer of the 3 inoculated cats averages 1:18 as compared to less than 1:2 for the 2 unvaccinated controls. One month later, all 5 cats are challenged intranasally with virulent FVR applied by droplets to each nostril (about 10,000–20,000 TCID$_{50}$/cat). The cats are observed for 2 weeks for evidence of clinical disease. All of the 3 vaccinated cats remain normal with no clinical disease or symptoms in contrast to the 2 unvaccinated controls which become very ill with FVR disease exhibiting typical symptoms such as febrile response, running eyes and nose, lack of appetite and general malaise. Two months after challenge, the antibody titer of all 5 animals is about the same (1:54), indicating the protection afforded the vaccinates and the successful challenge to the controls.

EXAMPLE III

Live virulent FVR virus cultured and isolated according to the procedure described by J. L. Bittle et al., ibid., and denoted by said investigators as an "F-2" isolate was serially passed 37 consecutive times in roller tube primary feline kidney tissue culture at 2–7 day intervals and at incubation temperatures of 35°–37° C. using the same culture medium described by Bittle et al. At the end of the 37th passage, the high degree of pathogenicity retained by the virus made it unsuitable for immunization purposes. However, attenuation of the virus to a suitable vaccine was accomplished upon subsequent passage, at lower incubation temperatures. Following the 37th passage, 44 additional serial passages (for a total of 81 passages) were then made at incubation temperatures of about 32° C.

A 0.2 ml inoculum from the 81st such passage, having a titer of $10^{5.0}$ TCID$_{50}$/ml (50 percent end point infectivity) as calculated by the ReedMuench method, was then added to monolayers of a feline diploid tongue cell line in tissue culture tubes (16×125 mm) and the serial passage procedure described in Example I was repeated for 7 consecutive passages followed by 3 terminal dilutions and 1 volume-increasing passage for a total of 11 serial passages. At the end of the 11th passage, the pool of bulk raw vaccine is harvested, identified (by serum neutralization tests with specific FVR goat antiserum) and titrated.

EXAMPLE IV

1 Ml of the vaccine prepared in Example III and having a virus titer at 35° C. of $10^{5.4}$ TCID$_{50}$/ml (determined by CPE) was administered intramuscularly to three susceptible cats which were previously determined to be sero-negative to FVR virus. Two other cats were maintained as unvaccinated controls. On the fourth day after inoculation, negative results of a throat swab test on all 5 cats was obtained indicating an absence of shedding of the virus. Two weeks after the initial inoculation date, one of the three vaccinated cats was given a second 1 ml injection intramuscularly. One month after the initial inoculation date, all five cats were challenged intranasally with virulent FVR virus applied by droplets to each nostril (10,000-20,000 TCID$_{50}$/cat). During the next two week observation period, all of the three vaccinated cats remained normal in contrast to the two unvaccinated cats which evidenced symptoms of FVR disease. The results showed that one inoculation of the subject vaccine produced a minimal antibody response whereas two inoculations induced a significantly higher response. The following antibody titers were observed:

TABLE 1

|  | Antibody Response | | |
| --- | --- | --- | --- |
|  | Pre-Vaccination | 1 Month After Vaccination | 2 Months After Challenge |
| Control 1 | 0 | 0 | 1:54 |
| Control 2 | 0 | 0 | 1:54 |
| Cat A | 0 | 1:18 | 1:54 |
| Cat B | 0 | 1:18 | 1:54 |
| Cat C* | 0 | 1:54 | 1:162 |

*Cat C received 2nd 1 ml injection 2 weeks after 1st injection.

EXAMPLE V

Larger pools of vaccine material were prepared after the 11th feline tongue passage described in Example III repeating the same method in flasks described therein for a total of 17 consecutive serial passage in feline tongue. 500 Ml of the virus material obtained from the 17th passage was added to 500 ml of N-Z amine lactose glutamate stabilizer and dispensed into standard vaccine vials (titer equaled $10^{4.6}$ TCID$_{50}$/ml) that were dried by conventional freeze-drying procedures. For inoculation purposes, the vials were reconstituted with 1 ml pyrogen-free sterile distilled water. 1 Ml of the thus-prepared vaccines were administered intramuscularly to two susceptible cats with one other unvaccinated cat maintained as a control. One week later, the two vaccinated cats were given an identical booster dose intramuscularly. Nine months after the initial inoculation, all 3 cats were challenged intranasally with virulent FVR virus applied by droplets to each nostril (10,000-20,000 TCID$_{50}$/cat). The cats were observed for 13 subsequent days for evidence of clinical disease. the two vaccinated cats each showed slight symptoms on 2 out of the 13 days whereas the unvaccinated control experienced severe clinical symptoms for 6 of the 13 days. One year after the initial inoculation, all 3 cats were rechallenged with FVR virus as before with no subsequent clinical disease symptoms being observed in any of the cats. In view of the foregoing, the long-term effect of the subject vaccine on the vaccinated cats was demonstrated. The lack of disease symptoms in the unvaccinated control cat after the second challenge was, as expected, due to the immunity derived from the natural infection caused by the first challenge.

EXAMPLE VI

Further evidence of the long-term efficacy of the subject vaccines was demonstrated in the following one-year challenge study. 1 Ml of the vaccine prepared in Example V was administered intramuscularly to 8 susceptible cats with 4 unvaccinated cats maintained as controls. All 12 cats were pre-tested and found to be sero-negative to FVR virus. One week later, the 8 vaccinated cats were given an identical booster dose intramuscularly. One year after the initial inoculation date, 3 cats were given a third identical booster dose I.M. Five days later, all 8 cats were challenged intranasally with virulent FVR virus applied by droplets to each nostril (10,000-20,000 TCID$_{50}$/cat). The cats were observed for 13 subsequent days for evidence of clinical disease. The following results were obtained:

TABLE 2

|  | No. of Days of Clinical Signs | Severity of Clinical Signs |
| --- | --- | --- |
| Control 1 | 9 | severe |
| 2 | 8 | severe |
| 3 | 8 | severe |
| 4 | 9 | severe |
| Cat A | 3 | slight |
| B | 3 | slight |
| C | 4 | slight |
| D | 1 | slight |
| E | 6 | slight |
| Cat F* | 0 | none |
| G* | 0 | none |
| H* | 3 | slight |

*Cats F, G and H received the 2 boosters.

In addition to the preparation of the instant vaccines from live virulent FVR virus obtained from infected cats, this invention is also concerned with the preparation of a FVR vaccine using the FVR virus that has been modified by the method heretofore described. It would be commercially impractical for the preparation of a vaccine to use as the starting material for each new batch of vaccine live virulent FVR virus obtained from infected cats and then go through the requisite serial passages in order to acquire the modified virus for use as a vaccine. This invention, therefore, embodies the method of preparing a FVR vaccine which comprises using as the starting virus one that has already been modified by serial passages in feline tissue cultures as previously described, that is, a "seed" virus from a master batch of attenuated virus. Accordingly, there is herein provided a process of preparing a feline viral rhinotracheitis vaccine which comprises propagating an attenuated FVR virus, which attenuated virus is produced by the process heretofore described, by sufficient serial passages at an incubation temperature of about 32°–37° C. in a nutrient fluid feline tissue culture medium which is non-toxic to said virus until said fluid medium contains from about $10^4$ to about $10^7$ tissue culture infectious doses of said attenuated virus per ml and harvesting the fluid vaccine.

By the use of the procedures described herein, a modified FVR virus can be readily cultivated in large quantities and in high concentrations. Using feline tissue culture propagated modified FVR virus in concentrations of at least about $10^4$, generally from about $10^4$ to about $10^7$, and preferably from about $10^{4.5}$ to about $10^{6.0}$, tissue culture infectious doses of virus per 1.0 ml of final vaccine, and by parenterally administering 1 ml of such vaccine to cats, there is stimulated in such vaccinated cats the production of protective FVR antibodies comparable to those produced by natural infections without producing the usual pathological symptoms of feline viral rhinotracheitis. The vaccinated cats are also able to resist challenges with the disease-producing virus.

A marked increase in the antibody response has been observed upon the parenteral administration of a second, and even a third or more, "booster" dose of the instant vaccines. For example, it has been found that beneficial results are obtained when a second intramuscular injection is given about one week following the initial vaccination. For best results, it is recommended that the second injection be given not sooner than about 2–3 weeks following the first injection. Excellent results have even been observed with a booster dose given up to 12 months later.

As a further feature of this invention, it has been found that enhancement of antibody production can be accomplished, in addition to the aforementioned parenteral administration of booster doses of the instant vaccines, by the exposure of cats, which have been previously immunized by parenteral administration of the instant vaccines, to FVR virus by the intranasal route, which FVR virus either has been modified according to the present invention or is in its non-modified virulent form.

Such intranasal instillation following parenteral vaccination produces significantly high levels of antibodies that persist for long periods of time. Furthermore, when such treated animals are challenged with virulent virus, the protection afforded is much more solid, as demonstrated by the lack of clinical disease symptoms after challenges with as high as 250,000 TCID$_{50}$/cat of virulent, non-modified FVR virus. F—best results, it is recommended that a sufficient time elapse for the cat to become sensitized after the initial parenteral vaccination in order to develop at least a minimal degree of immunity as reflected by increased antibody formation before subjecting the animal to the subsequent intranasal contact with FVR virus. Preferably, the intranasal instillation is given within 2–4 weeks following the initial parenteral vaccination although good results have been observed when the former is administered up to 12 months following the parenteral vaccination.

Intranasal instillation is readily accomplished by inhalation of the FVR virus either by conventional aerosol formulations sprayed into the nasal passages or by droplets applied to the outer nostrils or in the nasal passages. A suitable concentration of FVR virus, whether modified as described hereinbefore or in its live virulent unattenuated form, for intranasal instillation purposes following initial vaccination by parenteral administration is from about $10^3$ to about $10^6$ tissue culture infectious doses per ml.

It is believed that the initial vaccination by the parenteral route followed by contact with FVR virus, either modified or not, by the respiratory route constitutes a novel method of immunization against feline viral rhinotracheitis. Such method provides the animal with a humoral antibody response and a local immunity to the respiratory tract that is much more protective against the disease. Thus, a means is provided for effective, long-lasting protection against feline viral rhinotracheitis.

EXAMPLE VII

This example demonstrates a method of preparing a pool of live virulent FVR virus suitable for administration by the respiratory route after parenteral vaccination.

A. Tissues

Primary feline kidney tissue cultures (PFKTC) are harvested and grown at about 35° C. by the method described by J. L. Bittle et al., Amer. J. Vet. Res., 21, 547 (1960) employing conventional tissue culture techniques.

The Crandell feline kidney cell line (CrFK), referred to by Lee et al., Cornell Vet., 59, 539 (1969) is grown at about 37° C. in stationary tubes or bottles utilizing Minimum Essential Medium (MEM) with Earle's Balanced Salt Solution (BSS) and 10% fetal calf serum, 0.1% lactalbumin hydrolysate, 30 units penicillin, 30 mcg streptomycin and 2.5 mcg amphotericin. Upon completion of monolayer growth, the fluid medium is removed and a maintenance medium (same as above but with 1–2% fetal calf serum) is utilized at about 37° C.

B. Virus Pool 1.0 Milliliter portions of a primary feline kidney tissue culture medium consisting of 0.5% lactalbumin hydrolysate and 10% horse serum in Earle's BSS with 200 units penicillin and 200 mcg streptomycin per ml was allowed to stand in stationary tubes at about 35° C. until good growth of cells was observed. The fluid was then replaced by maintenance medium [same as before except with reduced (5%) horse serum] and inoculated with a 0.2 ml sample of live virulent FVR virus [identified as the "C-27" isolate by R. A. Crandell et al., Proc. Soc. Exptl. Biol. & Med., 97, 487 (1958)]. The inoculated medium was placed in a roller drum at about 35° C. and the virus harvested when approximately 80–90% of the cells exhibited cytopathogenic effects (CPE). This procedure was repeated for a total of 10 such serial passages. At the 10th passage, a 0.2 ml sample of material was inoculated into stationary tubes containing the CrFK cell line and incubated at about 35° C. until 80–90% CPE. Two similar passages in CrFK cell line were conducted in bottles for harvesting of a larger pool. After the 13th passage, the harvested pool, which had a titer of approximately $10^7$ TCID$_{50}$/ml, was stored at $-70°$ C. Dilutions of this material to appropriate concentrations were subsequently made for administration by the respiratory route.

EXAMPLE VIII

1 Ml of the vaccine prepared in Example III and having a virus titer at 35° C. of $10^{5.4}$ TCID$_{50}$/ml was administered intramuscularly to three susceptible cats which were previously determined to be sero-negative to FVR virus. Two other cats were maintained as unvaccinated controls. Eleven days after the initial inoculation date, one of the three vaccinated cats was given a second 1 ml injection intramuscularly. About 1 month after the initial inoculation date, all three vaccinated cats and the two unvaccinated controls were subjected to intranasal instillation of the live virulent FVR virus preparation obtained from Example VII and appropriately diluted. The head of each cat is tilted backwards and droplets totaling 250,000 TCID$_{50}$/cat of the virus are deposited in the nostrils using a 26 gauge needle and syringe. The following results were obtained, indicating a significantly higher antibody response and lack of clinical disease symptoms when intranasal administration of the virus follows parenteral vaccination.

TABLE 3

| | Antibody Response | | |
|---|---|---|---|
| | Titer at time of Intranasal Instillation | Titer After Intranasal Instillation** | Clinical Symptoms After Intranasal Instillation |
| Cat A* | 1:54 | 1:162 | none |
| Cat B | 1:18 | 1:54 | none |
| Cat C | 1:8 | 1:54 | none |
| Control 1 | <1:2 | 1:54 | severe |
| Control 2 | <1:2 | 1:54 | severe |

*Cat A received the two injections.
**Measurements taken 1 month after intranasal instillation.

EXAMPLE IX

A 1 ml injection I.M. of the vaccine prepared in Example V ($10^{4.6}$ TCID$_{50}$/ml titer) was given to seven susceptible cats which were previously determined to be sero-negative to FVR virus. A second similar injection was administered to all seven cats 15 days later. Three of the vaccinated cats were given an identical third injection 5 days prior to intranasal instillation with live virus. Two other cats were maintained as unvaccinated controls. About one year following the initial inoculation date, all seven vaccinated cats and the two unvaccinated controls were subjected to intranasal instillation of the live virulent FVR virus preparation obtained from Example VII and appropriately diluted. Each cat received 250,000 tissue culture infectious doses of the virus by droplets applied to the nostrils. The following results were obtained, indicating the long-term effectiveness occassioned by the parenteral plus intranasal routes of administration.

TABLE 4

| | Antibody Response | | |
|---|---|---|---|
| | Titer at Time of Intranasal Instillation | Titer After Intranasal Instillation* | Clinical Symptoms After Intranasal Instillation |
| Cat A | 1:15 | 1:290 | mild |
| Cat B | 1:15 | 1:417 | mild |
| Cat C | 1:7 | 1:96 | mild |
| Cat D | 1:22 | 1:200 | mild |
| Cat E** | 1:22 | 1:200 | none |
| Cat F** | 1:46 | 1:290 | none |
| Cat G** | 1:32 | 1:200 | very mild |
| Control 1 | <1:2 | 1:66 | severe |
| Control 2 | <1:2 | 1:22 | severe |

*Measurements taken 6 weeks after intranasal instillation.
**These cats received a total of 3 I.M. injections.

EXAMPLE X

A 1 ml injection I.M. of the vaccine prepared in Example V ($10^{4.6}$ TCID$_{50}$/ml titer) was given to two susceptible cats which were previously determined to be sero-negative to FVR virus. A second similar injection was administered to both cats 15 days later. About 9 months following the initial inoculation date, the two vaccinated cats were subjected to intranasal instillation of the live virulent FVR virus preparation obtained from Example VII and appropriately diluted. Each cat received 100,000 tissue culture infectious doses of the virus by droplets applied to the nostrils. Three months later all the cats were challenged intranasally with 250,000 TCID$_{50}$/cat of live FVR virus. The following results were obtained:

TABLE 5

| | Antibody Titer at Time of Intranasal Instillation | Antibody Titer at Time of Challenge | Clinical Symptoms 14 Days After Challenge | Antibody Titer Six Weeks After Challenge |
|---|---|---|---|---|
| Cat A | 1:7 | 1:45 | none | 1:138 |
| Cat B | 1:7 | 1:66 | none | 1:96 |

The foregoing Examples VIII through X demonstrate the feature of this invention whereby cats are afforded effective long-lasting immunization against FVR by the process which comprises first administering parenterally to a cat a vaccine of at least about $10^4$ tissue culture infectious doses of an attenuated feline viral rhinotracheitis virus, which virus was attenuated by at least 7 two- to seven-day serial passages through feline tissue cultures in a nutrient fluid at an incubation temperature of about 30°±2° C., followed by a subsequent administration to said cat by the respiratory route of from about $10^3$ to about $10^6$ tissue culture infectious doses of feline viral rhinotracheitis virus in its live virulent unattenuated form. Similar results are also obtainable with the respiratory administration of from about $10^3$ to about $10^6$ tissue culture infectious doses of feline viral rhinotracheitis virus which has been attenuated according to the methods of this invention.

What is claimed is:

1. A process of attenuating virulent feline viral rhinotracheitis virus which comprises propagating said virus for at least 7 two- to seven-day serial passages through feline tissue cultures in a nutrient fluid at an incubation temperature of about 30°±2° C.

2. A process of attenuating virulent feline viral rhinotracheitis virus for the production of a vaccine capable when injected into cats of immunizing them against feline viral rhinotracheitis which comprises introducing an inoculum of live infectious feline viral rhinotracheitis virus into a nutrient fluid culture medium which is non-toxic to said virus and contains viable feline tongue cells, and serially propagating said virus according to the process of claim 1.

3. A process of preparing a feline viral rhinotracheitis vaccine which comprises attenuating live infectious feline viral rhinotracheitis virus by serially propagating said virus according to the process of claim 1 until a virus titer of at least about $10^4$ tissue culture infectious doses of virus per milliliter is obtained and harvesting the thus-attenuated virus.

4. A process of preparing a feline viral rhinotracheitis vaccine which comprises attenuating live infectious feline viral rhinotracheitis virus by serially propagating said virus according to the process of claim 1 employing nutrient fluid cultures containing viable feline tongue cells until a virus of from about $10^4$ to about $10^7$ tissue culture infectious doses of virus per milliliter is obtained and harvesting the thus-attenuated virus.

5. A process of preparing a feline viral rhinotracheitis vaccine in dry solid form which comprises propagating live infectious feline viral rhinotracheitis virus obtained according to the process of claim 1 until a virus titer of at least about $10^4$ tissue culture infectious doses of attenuated virus per ml is obtained and drying at low temperature and thus-obtained attenuated virus-containing fluid.

6. A vaccine for immunizing susceptible cats by parenteral inoculation against feline viral rhinotracheitis and for increasing the antibody levels of thus-inoculated cats comprising at least about $10^4$ tissue culture infectious doses of an attenuated feline viral rhinotracheitis virus per unit dosage, which vaccine is capable of stimulating the production of protective feline viral rhinotracheitis antibodies comparable to those produced by natural infections when parenterally administered to non-immune cats but which does not produce the usual pathological symptoms of feline viral rhinotracheitis, said virus being attenuated by serially propagating virulent feline rhinotracheitis in feline tissue culture, at incubation temperature lower than that at which the virus remains virulent and does not attenuate in repeated serial passages through feline tissue culture, for a sufficient number of repeated serial passages until inoculation therewith of susceptible cats establishes that the virulence of the virus is so attenuated that upon intranasal administration to susceptible cats, the pathological symptoms of the disease are not observed in the inoculated cats, but there is formed therein antibodies against feline viral rhinotracheitis effective to immunize them against infectious viral rhinotracheitis.

7. A vaccine for immunizing cats against feline viral rhinotracheitis according to claim 6, in liquid form and comprising from about $10^4$ to about $10^7$ tissue culture infectious doses of the attenuated feline viral rhinotracheitis virus per ml.

8. A vaccine for immunizing cats against feline viral rhinotracheitis according to claim 6, in dry solid dosage form and containing from about $10^4$ tissue to about $10^7$ tissue culture infectious doses of an attenuated feline viral rhinotracheitis virus per dosage unit.

9. A method of immunizing cats against feline viral rhinotracheitis which comprises parenterally administering to a cat at least 1 ml of a vaccine according to claim 6.

10. A method of immunizing cats against feline viral rhinotracheitis which comprises parenterally administering to a cat at least 1 ml of a vaccine according to claim 7.

11. A method of immunizing cats against feline viral rhinotracheitis which comprises intramuscularly inoculating a cat with 1 ml of a vaccine according to claim 6 and at least one week later so inoculating said cat again with said vaccine.

12. A method of immunizing cats against feline viral rhinotracheitis which comprises intramuscularly inoculating a cat with 1 ml of a vaccine according to claim 6 and about 2-3 weeks later so inoculating said cat again with said vaccine.

13. A method of immunizing cats against feline viral rhinotracheitis which comprises intramuscularly inoculating a cat with 1 ml of a vaccine according to of claim 7 and at least one week later inoculating said cat again with said vaccine.

14. A method of immunizing cats against feline viral rhinotracheitis which comprises intramuscularly inoculating a cat with 1 ml of a vaccine prepared according to the process of claim 7 and about 2-3 weeks later inoculating said cat again with said vaccine.

15. A method of immunizing cats against feline viral rhinotracheitis which comprises parenterally administering to a cat a vaccine according to claim 6, and subsequently administering to said cat by the respiratory route from about $10^3$ to about $10^6$ tissue culture infectious doses of feline viral rhinotracheitis in its live virulent unattenuated form.

16. A method of immunizing cats against feline viral rhinotracheitis which comprises parenterally administering to a cat at least 1 ml of a vaccine according to claim 6 and about 2-4 weeks later administering to said cat by the respiratory route from about $10^3$ to about $10^6$ tissue culture infectious doses of feline viral rhinotracheitis virus in its live virulent unattenuated form.

17. A method of immunizing cats against feline viral rhinotracheitis which comprises parenterally administering to a cat at least 1 ml of a vaccine according to claim 6 and about 2-4 weeks later administering to said cat by the respiratory route from about $10^3$ to about $10^6$ tissue culture infectious doses of feline viral rhinotracheitis virus which has been attenuated according to the process of claim 1.

18. A method of immunizing cats against feline viral rhinotracheitis which comprises parenterally administering to a cat at least 1 ml of a vaccine according to claim 6 and about 2-4 weeks later administering an amount of vaccine to said cat by the respiratory route containing from about $10^3$ to about $10^6$ tissue culture infectious doses of feline viral rhinotracheitis virus which has been attenuated according to the process of claim 1.

19. A process of preparing a pool of attenuated feline viral rhinotracheitis for use in a feline viral rhinotracheitis vaccine which comprises propagating an attenuated feline rhinotracheitis virus obtained according to the process of claim 1, by sufficient serial passages through feline tissue cultures in a nutrient fluid at an incubation temperature of about 32°–37° C. until said fluid medium contains from about $10^4$ to about $10^7$ tissue culture infectious doses of attenuated virus per ml and harvesting the thus-propagated feline viral rhinotracheitis virus.

20. A process for the production of an attenuated live feline rhinotracheitis virus from a virulent live feline viral rhinotracheitis virus which will otherwise remain virulent and not attenuate in repeated passages through feline tissue cultures if maintained at 35° C., which comprises propagating said virus for a sufficient number of repeated serial passages through feline tissue cultures maintained at an incubation temperture within the range of from about 28° C. to about 32° C., until intranasal administration to susceptible cats establishes that the virulence of the virus is so attenuated that the pathological symptoms of the disease are no longer observed, with the formation in said vaccinated cats of antibodies against feline viral rhinotracheitis effective to immunize and completely protect said vaccinated cats against feline viral rhinotracheitis as evidenced by subsequent challenge of said vaccinated cats with virulent feline viral rhinotracheitis, and none developing the pathological symptoms of feline viral rhinotracheitis.

* * * * *